United States Patent [19]

Wahlstrom

[11] Patent Number: 5,386,449
[45] Date of Patent: Jan. 31, 1995

[54] METHOD AND A DEVICE FOR CARRYING OUT CONSTANT ENLARGEMENT IN PANORAMIC TOMOGRAPHIC X-RAY PHOTOGRAPHY

[75] Inventor: Matti Wahlstrom, Helsinki, Finland

[73] Assignee: Orion-Yhtyma Oy, Finland

[21] Appl. No.: 178,969

[22] Filed: Jan. 7, 1994

[30] Foreign Application Priority Data

Jan. 8, 1993 [FI] Finland .................. 930075

[51] Int. Cl.⁶ .............................. A61B 6/14
[52] U.S. Cl. ........................ 378/38; 378/39; 378/168
[58] Field of Search ............ 378/38, 39, 40, 167, 378/168, 170, 174, 175

[56] References Cited

U.S. PATENT DOCUMENTS

| 4,228,356 | 10/1990 | Cushman | 378/168 |
| 4,263,513 | 4/1981 | Palluet . | |
| 5,267,293 | 11/1993 | Virta | 378/38 |

FOREIGN PATENT DOCUMENTS

| 802928 | 3/1981 | Finland | G03B 42/02 |
| 833754 | 4/1985 | Finland | G03B 42/02 |
| 840412 | 8/1985 | Finland | A61B 6/14 |

*Primary Examiner*—David P. Porta
*Assistant Examiner*—Don Wong
*Attorney, Agent, or Firm*—Hayes, Soloway, Hennessey, Grossman & Hage

[57] ABSTRACT

The invention relates to a method used in the panoramic X-ray photography of a patient's set of teeth and a device for carrying out constant enlargement also in those spots (21) of the dental arch where the X-ray beam (12) is not perpendicular to the tangent (23) of the dental arch (20). Constant enlargement is achieved by selecting, on the film (13), a speed profile which follows the formula: $v_f = ((A+B/A) \times v_1 \times 1/\cos(b)$, where $v_f$ is the speed of the film, $v_1$ is a component of the propagation speed of the intersection of the X-ray beam and the spot to be photographed which is perpendicular to the X-ray beam, A is the distance between the focus of the X-ray source and the spot to be photographed, B is the distance between the spot to be photographed and the film, and b is the angle between the tangent (23) of the spot in question of the dental arch and the normal (22) of the X-ray beam.

4 Claims, 2 Drawing Sheets

METHOD AND A DEVICE FOR CARRYING OUT CONSTANT ENLARGEMENT IN PANORAMIC TOMOGRAPHIC X-RAY PHOTOGRAPHY

The invention relates to a method used in the panoramic X-ray photography of a patient's set of teeth and a device for carrying out constant enlargement also in those spots of the layer to be photographed where the X-ray beam does not go perpendicular to the tangent of the layer, but where the normal of the X-ray beam forms an angle with said tangent.

Tomography refers to the movement of the X-ray source, the patient and the X-ray film with respect to each other during X-ray photography. As a result of this, a certain level is very clearly photographed on the X-ray film while other areas which are photographed unclearly are left out of the photograph.

This technique for photographimg can be used to photograph the whole set of teeth of a patient on one film. The principle is that the narrow X-ray beam, which is in a rotational movement, goes through the head of a patient who is sitting still and photographs the dental arch on the film moving on the opposite side of the patient's head. The film moves at such a speed that a very sharp photograph is obtained of the layer which should be photographed, i.e. the teeth. The photographing is carried out by means of a device which includes a supporting arm, the X-ray source and the film casette being attached to its opposite ends so that they are situated on opposite sides of the patient's head so that the film is nearer to the dental arch of the patient to be photographed than the X-ray source.

It is essential to panoramic photography that the jaws with their sets of teeth are entirely photographed in the most orthogonal way, i.e., in a perpendicular projection. In this way, the photographing of the teeth in an overlapping way is prevented. Due to the form of the jaw, orthogonal photographing requires that the centre of rotation of the X-ray source is changed during the rotational movement.

Several solutions have been disclosed in which the location of the centre of rotation can be changed during the rotational movement. According to a solution, the centre of rotation of the X-ray source is made to rotate along an arched path. German patent publication DE-19 55 294 discloses a solution in which the movement of the centre of rotation of the X-ray source is effected in a manner defined by the dimensioning of a pair of cogwheels along an arched path. U.S. Pat. No. 3,636,349, consequently describes a panoramic X-ray installation in which the centre of rotation is made to move along an arched path during the rotation of the supporting arm. German patent DE-27 54 965 describes a panoramic X-ray installation which comprises a stationary frame part, a body which is mounted on bearings onto the frame part and moves linearly, i.e. a so-called linear part, a support arm rotatably mounted on bearings onto the linear part, the rotational axis of the support arm being perpendicular to the direction of movement of the linear body, the X-ray source and the film casette being attached to the opposite ends of the support arm so that they are situated on opposite sides of the patient's head. The mechanism includes members through which the centre of rotation is made to move, during the rotational movement of the support arm, along a line which is perpendicular to the axis of symmetry of the dental arch.

The current devices, however, cannot meet the prerequisite of orthogonalism on every spot of the dental arch; there are occasional spots where the X-ray beam is not perpendicular with respect to the tangent of the dental arch, whereby the normal of the X-ray beam forms, in the spot to be photographed, a certain angle (angle b) with the tangent of the dental arch. The speed of the film is usually defined by equation $v_f = ((A+B)/A) \times v_1$, where $v_f$ is the speed of the film, $v_1$ is a component of the propagation speed of the intersection of the X-ray beam and the spot to be photographed, which is perpendicular to the X-ray beam, A is the distance between the focus of the X-ray source and the spot to be photographed and B is the distance between the spot to be photographed and the film. If the tangent of the dental arch in the spot to be photographed does not coincide with the normal of the X-ray beam, but these together form an angle, the spot of the film to be photographed will appear smaller than the spots where the X-ray beam in the spot to be photographed forms a right angle with the tangent of the dental arch.

Thus some parts of the spots photographed by these solutions are not photographed in a completely right relationship with respect to each other, i.e., by constant enlargement. On the other hand, it is possible to provide constant enlargement, but it requires a complex and expensive arrangement. For instance, patent application FI-833754 describes a device in which the film magazine is able to move in the direction of the X-ray beam during the rotational movement of the support arm, i.e., the support arm actually moves in its axial direction with respect to its rotational axis. Using this radical movement it is possible to arrange it so that the film magazine, which would otherwise be, in the side area of the set of teeth, closer to the dental arch of the patient than in the front area of the set of teeth, stays at the desired distance from the set of teeth in the whole area of the dental arch.

Thus the purpose of this invention is a method for implementing constant enlargement in the panoramic X-ray photography of a patient's set of teeth, in which the panoramic X-ray installation comprises a support arm, the X-ray source and an image recorder being attached to the opposite ends of the support arm, whereby the support arm with the devices attached to its ends is made to rotate so that the X-ray source and the image recorder rotate around the patient's head. The method is characterized in that the speed of the image recorder is controlled during the photographing and dependant on both the location and the direction of the tangent of the spot in question of the dental arch, more specifically so that the speed of the image recorder is defined by equation $$v_f = ((A+B)/A) \times v_1 \times 1/\cos(b).$$

where
- A is the distance of the spot to be photographed from the focus of the X-ray source,
- B is the distance of the spot to be photographed from the image recorder,
- $v_1$ is a component of the propagation speed of the intersection of the X-ray beam and the spot to be photographed which is perpendicular to the X-ray beam, and
- b is the angle between the tangent of the spot to be photographed and the normal of the X-ray beam.

Another object of the invention is a device used in the method according to the invention for implementing constant enlargement in the panoramic X-ray photographing of a patient's set of teeth, the device comprising a support arm rotatably mounted on bearings, the X-ray source and the image recorder being attached to the opposite ends of the support arm, motors with their motion transmitting members to rotate the support arm, to convey the image recorder and, possibly, to transfer the bearing point of the support arm during the rotation, and to control the control devices of the motors of the processor provided with a memory. In the device according to the invention, the approximal form, specifically the assumed location of the teeth and the direction of the dental arch in each spot, is recorded in the memory of the processor before the photographing, and that the processor is adapted to control the driving motor of the image recorder so that the speed of the image recorder follows the formula $$v_f = ((A+B)/A)c \; v_1 \times 1/\cos(b).$$

where
- A is the distance of the spot to be photographed from the focus of the X-ray source,
- B is the distance of the spot to be photographed from the image recorder,
- $v_1$ is a component of the propagation speed of the intersection of the X-ray beam and the spot to be photographed which is perpendicular to the X-ray beam, and
- b is the angle between the tangent of the spot to be photographed and the normal of the X-ray beam.

The invention is disclosed in more detail in the following Figures.

Figure 1:
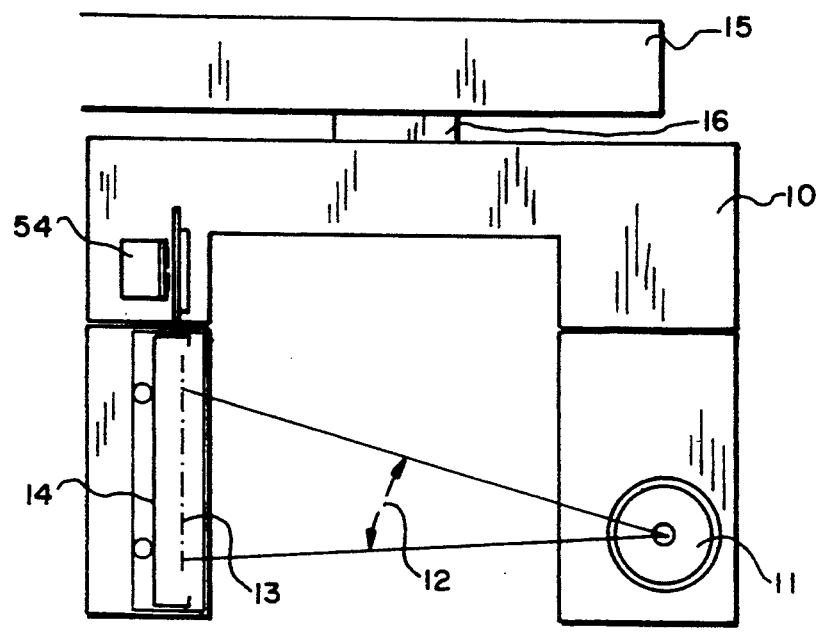
FIG. 1 shows the side view of the device used in panoramic X-ray photography.

In FIG. 1, X-ray source 11 is attached to one end of support arm 10 and film magazine 14 containing film 13 is attached to the other end of the support arm. The X-ray beam directed to the film from the X-ray source is marked with reference number 12. The support arm is connected with shaft 16 to the x, y slide moving from frame 15 and not shown here, the slide enabling the transferring of the centre of rotation of the support arm on the x, y level. Motor 54 is responsible for pulling the film at the desired speed. This arrangement is well-known to those skilled in the art, therefore is not expained here in more detail.

Figure 2:
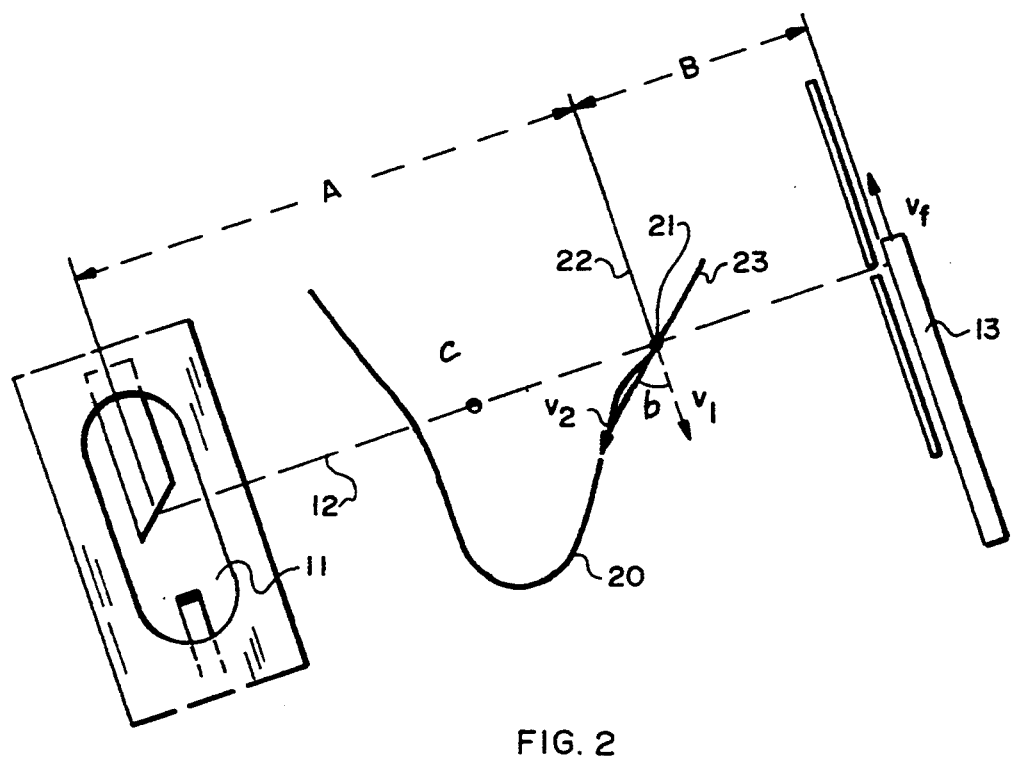
FIG. 2 shows a top view of the X-ray source, the film magazine and the dental arch to be photographed.

FIG. 2 shows diagrammatically the situation where X-ray beam 12 directed to film 13 from X-ray source 11 is not perpendicular to tangent 23 of dental arch 20 in spot 21 to be photographed, but normal 22 of X-ray beam 12 forms angle b with tangent 23. The momentary centre of rotation c of the support arm can be transferred on the x, y level. Because the speed $v_f$ of the film is conventionally defined by equation $v_f = ((A+B)/A) \times v_1$, where $(A+B)/A$ is the ratio of enlargement, and $v_1$ is a component of the propagation speed of the intersection of the X-ray beam and the spot to be photographed which is perpendicular to the X-ray beam, the part of the dental arch photographed in this spot will appear, on the film, narrower than those parts on which the X-ray beam hits the tangent of the dental arch perpendicularly. This drawback is eliminated according to the invention by correcting the speed of the image recorder $(A+B)/A \times v_1$ by coefficient $1/\cos(b)$, whereby the corrected speed corresponds to the real speed v2 of the intersection of the X-ray beam and the spot to be photographed. Thus, by defining the speed of the film according to equation $v_f = ((A+B)/A) \times v_1 \times 1/\cos(b)$, constant enlargement is obtained in every spot of the dental arch. In practice, the speed according to the diagram can be achieved so that the form of the dental arch is approximated to the memory of the processor beforehand, for instance, as a sufficient set of values of A, B and b, or in the form of a mathematical curve which is suitably chosen, whereby the processor uses these values, or preferably the speed values, which are already calculated on that basis, during the photographing. A certain range of preselected "design jaws" can be used, for instance, from which the user of the machine then chooses, according to the patient, the most suitable one to be recorded as the base values in the memory of the processor. After the initial adjustment of the support arm with respect to the patient is carried out, the design follows fairly precisely the real form of the dental arch. On the other hand, different ways to measure the form of the dental arch of a patient in advance are known from before.

Figure 3:
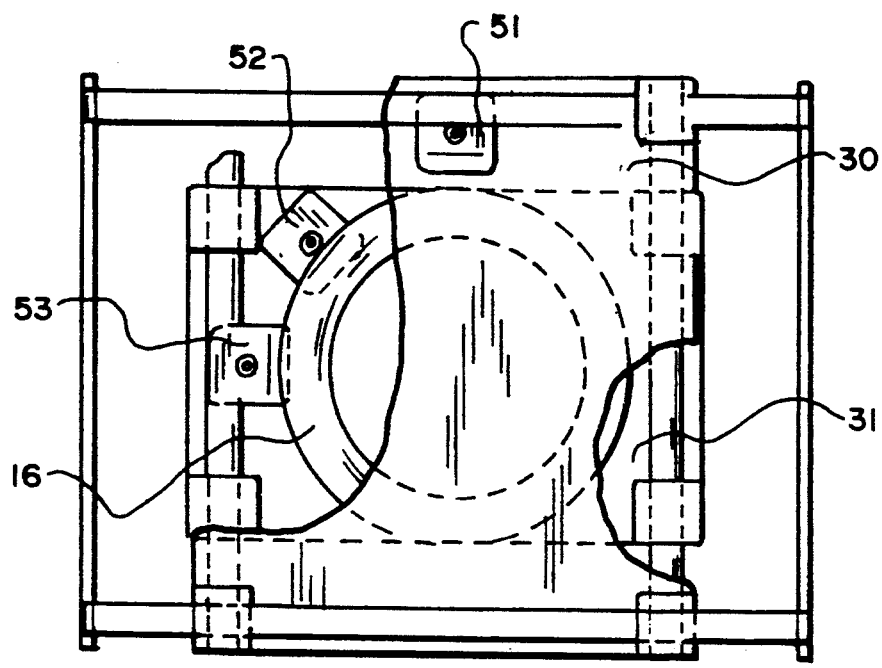
FIG. 3 shows a top view of the x, y slide of FIG. 1.

FIG. 3 is a top view of the x, y slide in frame 15. The slide comprises levels 30 and 31 which move perpendicular to each other in the frame and which are moved by motors 51 and 53, respectively. The presetting of the arm with respect to the patient can also be made by them before starting the photographing. Motor 52 is responsible for the rotational movement of the support arm. The tube-like shaft of the support arm is marked by reference number 16, the head supporting members (not shown) of the patient extending through the shaft in a manner known per se.

Figure 4:
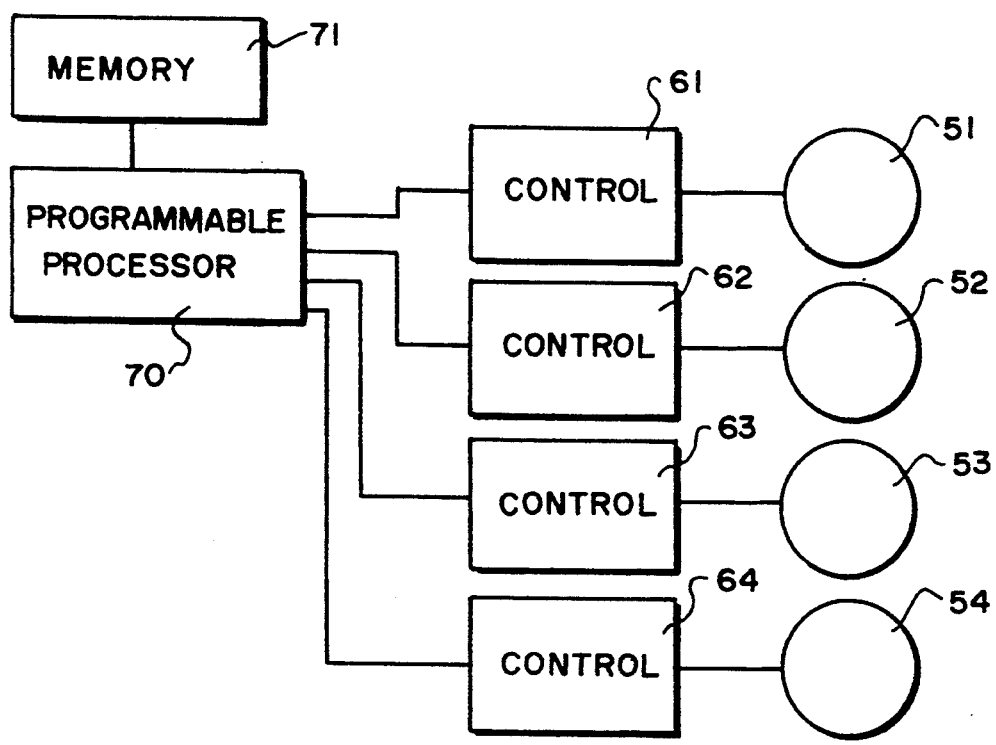
FIG. 4 shows schematically the motors and the adjusters of the device.

FIG. 4 shows the motors of the device with their adjusters. Programmable processor 70 provided with memory 71 controls motors 51-54 through control devices 61-64.

It is clear to those skilled in the art that different applications of the invention can vary within the claims disclosed hereafter.

I claim:

1. A method for carrying out constant enlargement in the panoramic X-ray photographing of a patient using a panoramic x-ray installation, where the panoramic X-ray installation comprises a support arm (10), an X-ray source (11) and an image recorder (13) being attached to the opposite ends of the support arm, whereby the support arm is made to rotate so that the x-ray source and the image recorder rotate around the patient's head, characterized in that the speed of the image recorder is controlled during the photographing to be depenant on both the location of and the direction of the tangent of a spot in question of a layer to be photographed such that the speed of the image recorder is defined by equation;

$$V_f = ((A+B)/A) \times V_1 / \cos(b);$$

where
- $V_f$ is the speed of the recorder,
- A is the distance of the spot to be photographed from the focus of the X-ray source,
- B is the distance of the spot to be photographed from the image recorder, V₁ is a component of the propagation speed of the intersection of an X-ray beam and the spot to be photographed which is perpendicular to the X-ray beam, and b is the angle between the tangent of the spot to be photographed and the normal of the x-ray beam.

2. A method according to claim 1, characterized in that the approximated form of the layer to be photographed, i.e., both the location and the direction of each spot, is recorded in advance in the memory of the processor controlling the panoramic X-ray installation, whereby the processor controls the drive motor (54) of the image recorder in accordance with said equation.

3. A method according to claim 1, characterized in that the layer to be photographed is a dental arch of the patient and the image recorder is a film (13) in a magazine (14).

4. A device for carrying out constant enlargement in the panoramic X-ray photography of a patient, the device comprising a suport arm (10) rotatably mounted on bearings, an X-ray source (11) and an image recorder being attached to the opposite ends of the support arm, motors (51-54) with movement transmitting member for rotating the support arm and for conveying the image recorder, and a processor (70) provided with a memory (71) for controlling control devices (61-64) of the motors (51-54), characterized in that the approximal form of a layer to be photographed is recorded in the memory (71) of the processor before the photographinig, and that the processor (70) is adapted to control the driving motors (54) of the image recorder so that the speed of the recorder follows the formula:

$$V_f = ((A+B)/A) \times V_1 \times 1/\cos(b);$$

where $V_f$ is the speed of the recorder,

A is the distance of the spot to be photographed from the focus of the X-ray source, B is the distance of the spot to be photographed from the image recorder, V₁ is a component of the propagation speed of the intersection of an X-ray beam and the spot to be photographed which is perpendicular to the X-ray beam, and b is the angle between the tangent of the spot to be photographed and the normal of the x-ray beam.

* * * * *

UNITED STATES PATENT AND TRADEMARK OFFICE
CERTIFICATE OF CORRECTION

PATENT NO. : 5,386,449
DATED      : January 31, 1995
INVENTOR(S): Matti Wahlstrom It is certified that error appears in the above-indentified patent and that said Letters Patent is hereby corrected as shown below:

Claim 1, Col. 4, Line 56, "depenant" should be --dependant--

Claim 1, Col. 4, Line 61, after "$V_1$" insert --X 1--

Claim 4, Col. 5, Line 20, "suport" should be --support--

Claim 4, Col. 6, Line 5, "photographinig" should be --photographing--

Signed and Sealed this

Eighteenth Day of April, 1995

Attest:

BRUCE LEHMAN

*Attesting Officer*  *Commissioner of Patents and Trademarks*